(12) United States Patent
Jähne et al.

(10) Patent No.: US 6,288,094 B2
(45) Date of Patent: Sep. 11, 2001

(54) POLYCYCLIC THIAZOL-2-YLIDENE AMINES, PROCESSES FOR THEIR PREPARATION AND THEIR USE AS MEDICAMENTS

(75) Inventors: Gerhard Jähne; Karl Geisen, both of Frankfurt; Hans-Jochen Lang, Hofheim; Martin Bickel, Bad Homburg, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/774,053

(22) Filed: Jan. 31, 2001

Related U.S. Application Data

(62) Division of application No. 09/500,464, filed on Feb. 9, 2000, now Pat. No. 6,207,689.

(30) Foreign Application Priority Data

Feb. 26, 1999 (DE) .............................................. 199 08 536

(51) Int. Cl.$^7$ ...................... A61K 31/429; C07D 513/04
(52) U.S. Cl. .................. 514/366; 548/149; 544/247; 540/555; 514/257; 514/219
(58) Field of Search ................................... 514/366, 257, 514/219; 548/149; 544/247; 540/555

(56) References Cited

U.S. PATENT DOCUMENTS

| | | | |
|---|---|---|---|
| 3,507,868 | * | 4/1970 | Manning ............................... 260/251 |
| 4,174,397 | * | 11/1979 | Knabe et al. ......................... 424/270 |
| 5,869,492 | * | 2/1999 | Kerrigan et al. ...................... 514/258 |

OTHER PUBLICATIONS

V.P. Arya et al., "Synthesis of New Heterocycles: Part III*—Syntheses of Certain Novel Condensed Imidazo [2,1–b] thiazoles & Thiazolo [3,2–a] pyrimidines", Indian Journal of Chemistry, vol. 9, pp. 1204–1208, Nov. 1971.*

George DeStevens et al., "Investigations in Heterocycles. II. Unsymmetrical Ureas, Thiourease and Related Thiazolines.", Journal of Organic Chemistry, vol. 23, pp. 114–116, Jan. 1958.*

P. Tyle, "Iontophoretic Devices for Drug Delivery", Pharmaceutical Research, 1986, 3 (6): pp. 318–326.*

* cited by examiner

*Primary Examiner*—Charanjit S. Aulakh
(74) *Attorney, Agent, or Firm*—Heller Ehrman White & McAulife LLP

(57) ABSTRACT

The invention relates to polycyclic thiazolidin-2-ylidene amines and their physiologically tolerated salts and physiologically functional derivatives.

Polycyclic thiazolidin-2-ylidene amines of the formula I,

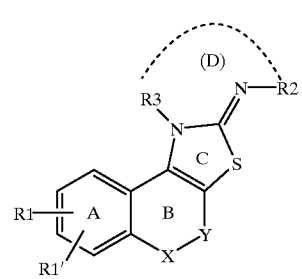

in which the radicals have the stated meanings, and their physiologically tolerated salts and processes for their preparation are described. The compounds are suitable, for example as anorectics and in the treatment or prophylaxis of type II diabetes.

13 Claims, No Drawings

POLYCYCLIC THIAZOL-2-YLIDENE AMINES, PROCESSES FOR THEIR PREPARATION AND THEIR USE AS MEDICAMENTS

This application is a divisional of Ser. No. 09/500,464 filed Feb. 9, 2000, U.S. Pat. No. 6,207,689.

BACKGROUND OF THE INVENTION

The invention relates to polycyclic thiazol-2-ylidene amines and to their physiologically tolerated salts and physiologically functional derivatives.

U.S. Pat. No. 3,507,868 has described tetracyclic imidazo[2,1-b]thiazoles and thiazolo[3,2-a]pyrimidines which are unsubstituted in ring A and have an anorectic effect.

The invention was based on the object of providing further compounds which display a therapeutically utilizable anorectic effect. In this connection, the object was also in particular to find compounds for which the anorectic effect is increased by comparison with the compounds of U.S. Pat. No. 3,507,868 and with which fewer side effects occur.

SUMMARY OF THE INVENTION

The invention relates to compounds of the formula I

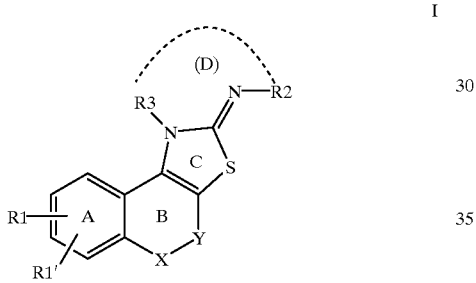

in which

Y is a direct linkage, —$CH_2$— or —$CH_2$—$CH_2$—;

X is $CH_2$, CH-phenyl, O or S;

R1 is F, Cl, Br, I, $CF_3$, $NO_2$, CN, COOH, COO($C_1$–$C_6$) alkyl, $CONH_2$, CONH($C_1$–$C_6$)alkyl, CON[($C_1$–$C_6$)alkyl]$_2$, ($C_1$–$C_6$)-alkyl, ($C_2$–$C_6$)-alkenyl, ($C_2$–$C_6$)-alkynyl, O—($C_2$–$C_6$)-alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, NH—CO—$CH_3$ or N(COOC$H_2$Ph)$_2$), $SO_2$—$NH_2$, $SO_2$NH($C_1$–$C_6$)-alkyl, $SO_2$N[($C_1$–$C_6$)-alkyl]$_2$, S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C_6$)-alkyl, $SO_2$—($CH_2$)$_n$-phenyl (where n is 0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$), $NH_2$, NH—($C_1$–$C_6$)-alkyl, N(($C_1$–$C_6$)-alkyl)$_2$, NH($C_1$–$C_7$)-acyl, phenyl, biphenylyl, O—($CH_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl ring may be independently optionally substituted up to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R1' is H, F, Cl, Br, I, $CF_3$, $NO_2$, CN, COOH, COO($C_1$–$C_6$) alkyl, $CONH_2$, CONH($C_1$–$C_6$)alkyl, CON[($C_1$–$C_6$)alkyl]$_2$, ($C_1$–$C_6$)-alkyl, ($C_2$–$C_6$)-alkenyl, ($C_2$–$C_6$)-alkynyl, O—($C_2$–$C_6$)-alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, NH—CO—$CH_3$ or N(COOC$H_2$Ph)$_2$), $SO_2$—$NH_2$, $SO_2$NH($C_1$–$C_6$)-alkyl, $SO_2$N[($C_1$–$C_6$)-alkyl]$_2$, S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C_6$)-alkyl, $SO_2$—($CH_2$)$_n$-phenyl (where n is 0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$), $NH_2$, NH—($C_1$–$C_6$)-alkyl, N(($C_1$–$C_6$)-alkyl)$_2$, NH($C_1$–$C_7$)-acyl, phenyl, biphenylyl, O—($CH_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be independently optionally substituted up to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), 1,2,3-triazol-5-yl (wherein the triazole ring may be optionally substituted in position 1, 2 or 3 by methyl or benzyl) or tetrazol-5-yl, (wherein the tetrazole ring may be optionally substituted in position 1 or 2 by methyl or benzyl);

R2 is ($C_1$–$C_6$)-alkyl, ($CH_2$)$_n$—COOH (where n is 1–4), ($C_3$–$C_6$)-cycloalkyl, ($CH_2$)$_n$-phenyl, ($CH_2$)$_n$-thienyl, ($CH_2$)$_n$-pyridyl or ($CH_2$)$_n$-furyl (where n is 0–5 and the phenyl, thienyl, pyridyl or furyl may each be substituted up to two times by Cl, F, CN, $CF_3$, ($C_1$–$C_3$)-alkyl, OH or O—($C_1$–$C_6$)-alkyl);

R3 is ($C_1$–$C_6$)-alkyl, ($CH_2$)$_n$—COOH (where n is 1–4), ($C_3$–$C_6$)-cycloalkyl, ($CH_2$)$_n$-phenyl, ($CH_2$)$_n$-thienyl, ($CH_2$)$_n$-pyridyl or ($CH_2$)$_n$-furyl (where n is 0–5 and the phenyl, thienyl, pyridyl or furyl may each be substituted up to two times by Cl, F, CN, $CF_3$, ($C_1$–$C_3$)-alkyl, OH or O—($C_1$–$C_6$)-alkyl); or R2 and R3 together form a —$CH_2$—$CH_2$—, —$CH_2$—C($CH_3$)$_2$—, —$CH_2$—$CH_2$—$CH_2$— or —$CH_2$—$CH_2$—$CH_2$—$CH_2$— group;

and their physiologically tolerated salts and physiologically functional derivatives.

The invention also relates to pharmaceutical compositions containing the compounds of formula I and pharmaceutically acceptable carriers. Also pharmaceutical compositions containing the compounds of formula I in combination with at least one additional anorectic agents are contemplated. The invention envisages treatment of obesity via administration of compounds of formula I. Methods of treatment for type II diabetes are also contemplated.

DETAILED DESCRIPTION OF THE PREFERRED EMBODIMENTS

The invention relates to compounds of the formula I

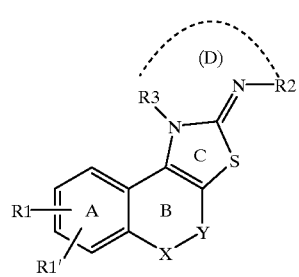

in which

Y is a direct linkage, —$CH_2$— or —$CH_2$—$CH_2$—;

X is $CH_2$, CH-phenyl, O or S;

R1 is F, Cl, Br, I, $CF_3$, $NO_2$, CN, COOH, COO($C_1$–$C_6$)alkyl, $CONH_2$, CONH($C_1$–$C_6$)alkyl, CON[($C_1$–$C_6$)alkyl]$_2$, ($C_1$–$C_6$)-alkyl, ($C_2$–$C_6$)-alkenyl, ($C_2$–$C_6$)-alkynyl, O—($C_2$–$C_6$)-alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, NH—CO—$CH_3$ or N(COOCH$_2$Ph)$_2$), $SO_2$—$NH_2$, $SO_2$NH($C_1$–$C_6$)-alkyl, $SO_2$N[($C_1$–$C_6$)-alkyl]$_2$, S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C_6$)-alkyl, $SO_2$—($CH_2$)$_n$-phenyl (where n is 0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$), $NH_2$, NH—($C_1$–$C_6$)-alkyl, N(($C_1$–$C_6$)-alkyl)$_2$, NH($C_1$–$C_7$)-acyl, phenyl, biphenylyl, O—($CH_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl ring may be independently optionally substituted up to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), 1,2,3-triazol-5-yl (wherein the triazole ring may be optionally substituted in position 1, 2 or 3 by methyl or benzyl) or tetrazol-5-yl, (wherein the tetrazole ring may be optionally substituted in position 1 or 2 by methyl or benzyl);

R1' is H, F, Cl, Br, I, $CF_3$, $NO_2$, CN, COOH, COO($C_1$–$C_6$)alkyl, $CONH_2$, CONH($C_1$–$C_6$)alkyl, CON[($C_1$–$C_6$)alkyl]$_2$, ($C_1$–$C_6$)-alkyl, ($C_2$–$C_6$)-alkenyl ($C_2$–$C_6$)-alkynyl, O—($C_2$–$C_6$)-alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, NH—CO—$CH_3$ or N(COOCH$_2$Ph)$_2$), $SO_2$—$NH_2$, $SO_2$NH($C_1$–$C_6$)-alkyl, $SO_2$N[($C_1$–$C_6$)-alkyl]$_2$, S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C_6$)-alkyl, $SO_2$—($CH_2$)$_n$-phenyl (where n is 0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$), $NH_2$, NH—($C_1$–$C_6$)-alkyl, N(($C_1$–$C_6$)-alkyl)$_2$, NH($C_1$–$C_7$)-acyl, phenyl, biphenylyl, O—($CH_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be independently optionally substituted up to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), 1,2,3-triazol-5-yl (wherein the triazole ring may be optionally substituted in position 1, 2 or 3 by methyl or benzyl) or tetrazol-5-yl, (wherein the tetrazole ring may be optionally substituted in position 1 or 2 by methyl or benzyl);

R2 is ($C_1$–$C_6$)-alkyl, ($CH_2$)$_n$-COOH (where n is 1–4), ($C_3$–$C_6$)-cycloalkyl, ($CH_2$)$_n$-phenyl, ($CH_2$)$_n$-thienyl, ($CH_2$)$_n$-pyridyl or ($CH_2$)$_n$-furyl (where n is 0–5 and the phenyl, thienyl, pyridyl or furyl may each be substituted up to two times by Cl, F, CN, $CF_3$, ($C_1$–$C_3$)-alkyl, OH or O—($C_1$–$C_6$)-alkyl);

R3 is ($C_1$–$C_6$)-alkyl, ($CH_2$)$_n$-COOH (where n is 1–4), ($C_3$–$C_6$)-cycloalkyl, ($CH_2$)$_n$-phenyl, ($CH_2$)$_n$-thienyl, ($CH_2$)$_n$-pyridyl or ($CH_2$)$_n$-furyl (where n is 0–5 and the phenyl, thienyl, pyridyl or furyl may each be substituted up to two times by Cl, F, CN, $CF_3$, ($C_1$–$C_3$)-alkyl, OH or O—($C_1$–$C_6$)-alkyl); or R2 and R3 together form a —$CH_2$—$CH_2$—, —$CH_2$—C($CH_3$)$_2$—, —$CH_2$—$CH_2$—$CH_2$— or —$CH_2$—$CH_2$—$CH_2$—$CH_2$— group;

and their physiologically tolerated salts and physiologically functional derivatives.

In a preferred embodiment, compounds of formula I are those in which one or more radical(s) has or have the following meaning:

Y is a direct linkage, —$CH_2$— or —$CH_2$—$CH_2$—;

X is $CH_2$ or O;

R1 is F, Cl, Br, I, $CF_3$, $NO_2$, CN, COOH, COO($C_1$–$C_6$)alkyl, $CONH_2$, CONH($C_1$–$C_6$)alkyl, CON[($C_1$–$C_6$)alkyl]$_2$, ($C_1$–$C_6$)-alkyl, ($C_2$–$C_6$)-alkenyl, ($C_2$–$C_6$)-alkynyl, O—($C_2$–$C_6$)-alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, NH—CO—$CH_3$ or N(COOCH$_2$Ph)$_2$), $SO_2$—$NH_2$, $SO_2$—($C_1$–$C_6$)-alkyl, $SO_2$—($CH_2$)$_n$-phenyl (where n is 0–6 and the phenyl radical may be substituted up to two times by F, Cl, OH, $CF_3$, CN, $OCF_3$, O—($C_1$–$C_6$)-alkyl, ($C_1$–$C_6$)-alkyl or $NH_2$), $NH_2$NH—($C_1$–$C_6$)-alkyl, N(($C_1$–$C_6$)-alkyl)$_2$, NH($C_1$–$C_7$)-acyl, phenyl, biphenylyl, O—($CH_2$)$_n$-phenyl (where n is 0–6), 1- or 2-naphthyl, 2-, 3- or 4-pyridyl, 2- or 3-furanyl, 2- or 3-thienyl (wherein phenyl, biphenylyl, naphthyl, pyridyl, furanyl or thienyl rings each may be independently optionally substituted once or twice by F, Cl, Br, I, OH, $CF_3$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), 1,2,3-triazol-5-yl (wherein the triazole ring may be optionally substituted in position 1, 2 or 3 by methyl or benzyl) or tetrazol-5-yl, (wherein the tetrazole ring may be optionally substituted in position 1 or 2 by methyl or benzyl);

R1' is H, F, Cl, I, $CF_3$, CN, COOH, COO($C_1$–$C_6$)alkyl, $CONH_2$, CONH($C_1$–$C_6$)alkyl, CON[($C_1$–$C_6$)alkyl]$_2$, ($C_1$–$C_6$)-alkyl, ($C_2$–$C_6$)-alkenyl, O—($C_2$–$C_6$)-alkyl (where one, more than one or all hydrogens(s) in the alkyl radicals may be replaced by fluorine, or one hydrogen may be replaced by OH, OC(O)$CH_3$, OC(O)H, O—$CH_2$—Ph, $NH_2$, NH—CO—$CH_3$ or N(COOCH$_2$Ph)$_2$), SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl (where n is 0–6 and the phenyl radical may be substituted up to two times by F, Cl, OH, CF$_3$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, fuiranyl or thienyl rings may be independently optionally substituted once or twice by F, Cl, I, OH, CF$_3$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 is (C$_1$–C$_6$)-alkyl, (CH$_2$)$_n$—COOH (where n is 1–4), (C$_3$–C$_6$)-cycloalkyl, (CH$_2$)$_n$-phenyl, (CH$_2$)$_n$-thienyl, (CH$_2$)$_n$-pyridyl or (CH$_2$)$_n$-furyl (where n is 0–5 and the phenyl, thienyl, pyridyl or furyl may each be substituted up to two times by Cl, F, CN, CF$_3$, (C$_1$–C$_3$)-alkyl, OH or O—(C$_1$–C$_6$)-alkyl);

R3 is (C$_1$–C$_6$)-alkyl, (CH$_2$)$_n$—COOH (where n is 1–4), (C$_3$–C$_6$)-cycloalkyl, (CH$_2$)$_n$-phenyl, (CH$_2$)$_n$-thienyl, (CH$_2$)$_n$-pyridyl or (CH$_2$)$_n$-furyl (where n is 0–5 and the phenyl, thienyl, pyridyl or furyl may each be substituted up to two times by Cl, F, CN, CF$_3$, (C$_1$–C$_3$)-alkyl, OH or O—(C$_1$–C$_6$)-alkyl); or R2 and R3 together form a —CH$_2$—CH$_2$—, —CH$_2$—C(CH$_3$)$_2$— or —CH$_2$—CH$_2$—CH$_2$— group; and their physiologically tolerated salts and physiologically functional derivatives.

In a particularly preferred embodiment are compounds of the formula I in which one or more radical(s) has or have the following meaning:

Y is a direct linkage or —CH$_2$—;

X is CH$_2$, O or S;

R1 is F, Cl, Br, CF$_3$, NO$_2$, CN, COOH, COO(C$_1$–C$_6$) alkyl, CONH$_2$, CONH(C$_1$–C$_6$)alkyl, CON[(C$_1$–C$_6$)alkyl]$_2$, (C$_1$–C$_6$)-alkyl, (C$_2$–C$_6$)-alkenyl, (C$_2$–C$_6$)-alkynyl, O—(C$_2$–C$_6$)-alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$—(C$_1$–C$_6$)-alkyl, SO$_2$—(CH$_2$)$_n$-phenyl (where n is 0–6 and the phenyl radical may be substituted up to two times by F, Cl, OH, CF$_3$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (where n is 0–6), 1- or 2-naphthyl, 2-, 3- or 4-pyridyl, 2- or 3-furanyl, 2- or 3-thienyl, (wherein the phenyl, biphenylyl, naphthyl, pyridyl, furanyl or thienyl rings may be independently optionally substituted once or twice by F, Cl, Br, I, OH, CF$_3$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R1' is H, F, Cl, Br, CF$_3$, CN, COOH, COO(C$_1$–C$_6$)alkyl, CONH$_2$, CONH(C$_1$–C$_6$)alkyl, CON[(C$_1$–C$_6$)alkyl]$_2$, (C$_1$–C$_6$)-alkyl, (C$_2$–C$_6$)-alkenyl, (C$_2$–C$_6$)-alkynyl, O—(C$_2$–C$_6$)-alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl (where n is 0–6 and the phenyl radical may be substituted up to two times by F, Cl, OH, CF$_3$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (where n is 0–6), 1- or 2-naphthyl, 2-, 3- or 4-pyridyl, 2- or 3-furanyl, 2- or 3-thienyl, wherein the phenyl, biphenylyl, naphthyl, pyridyl, furanyl or thienyl rings may be independently optionally substituted once or twice by F, Cl, I, OH, CF$_3$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 is (C$_1$–C$_6$)-alkyl, (CH$_2$)$_n$—COOH (where n is 1–4), (C$_3$–C$_6$)-cycloalkyl, (CH$_2$)$_n$-phenyl, (CH$_2$)$_n$-thienyl, (CH$_2$)$_n$-pyridyl or (CH$_2$)$_n$-furyl (where n is 0–5 and the phenyl, thienyl, pyridyl or furyl may each be substituted up to two times by Cl, F, CN, CF$_3$, (C$_1$–C$_3$)-alkyl, OH or O—(C$_1$–C$_6$)-alkyl);

R3 is (C$_1$–C$_6$)-alkyl, (CH$_2$)$_n$—COOH (where n is 1–4), (C$_3$–C$_6$)-cycloalkyl, (CH$_2$)$_n$-phenyl, (CH$_2$)$_n$-thienyl, (CH$_2$)$_n$-pyridyl or (CH$_2$)$_n$-furyl (where n is 0–5 and the phenyl, thienyl, pyridyl or furyl may each be substituted up to two times by Cl, F, CN, CF$_3$, (C$_1$–C$_3$)-alkyl, OH or O—(C$_1$–C$_6$)-alkyl);

and their physiologically tolerated salts and physiologically functional derivatives.

Most particularly preferred are compounds of the formula I in which one or more radical(s) has or have the following meaning:

Y is a direct linkage;

X is CH$_2$ or O;

R1 is F, Cl, Br, CF$_3$, NO$_2$, CN, COOH, COO(C$_1$–C$_6$) alkyl, CONH$_2$, CONH(C$_1$–C$_6$)alkyl, CON[(C$_1$–C$_6$)alkyl]$_2$, (C$_1$–C$_6$)-alkyl, (C$_2$–C$_6$)-alkenyl, O—(C$_2$–C$_6$)-alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$—(C$_1$–C$_6$)-alkyl, SO$_2$—(CH$_2$)$_n$-phenyl (where n is 0–6 and the phenyl radical may be substituted up to two times by F, Cl, OH, CF$_3$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be independently optionally substituted once or twice by F, Cl, OH, CF$_3$, CN, OCF$_3$, O—(C$_1$–C$_6$)-alkyl, (C$_1$–C$_6$)-alkyl, NH$_2$, NH(C$_1$–C$_6$)- alkyl, N(($C_1$–$C_6$)-alkyl)$_2$, $SO_2$—$CH_3$, COOH, COO—($C_1$–$C_6$)-alkyl or $CONH_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R1' is H, F, Cl, $CF_3$, CN, COOH, COO($C_1$–$C_6$)alkyl, $CONH_2$, CONH($C_1$–$C_6$)alkyl, CON[($C_1$–$C_6$)alkyl]$_2$, ($C_1$–$C_6$)-alkyl, ($C_2$–$C_6$)-alkenyl, ($C_2$–$C_6$)-alkynyl, O—($C_2$–$C_6$)-alkyl (where one, more than one or all hydrogen(s) in the alkyl radicals may be replaced by fluorine, or one hydrogen may be replaced by OH, $OC(O)CH_3$, OC(O)H, O—$CH_2$—Ph, $NH_2$, NH—CO—$CH_3$ or N($COOCH_2Ph$)$_2$), $SO_2$NH ($C_1$–$C_6$)-alkyl, $SO_2$N[($C_1$–$C_6$)-alkyl]$_2$, $SO_2$—($C_1$–$C_6$)-alkyl, $SO_2$—($CH_2$)$_n$-phenyl (where n is 0–6 and the phenyl radical may be substituted up to two times by F, Cl, OH, $CF_3$, CN, $OCF_3$, O—($C_1$–$C_6$)-alkyl, ($C_1$–$C_6$)-alkyl or $NH_2$), $NH_2$, NH—($C_1$–$C_6$)-alkyl, N(($C_1$–$C_6$)-alkyl)$_2$, NH($C_1$–$C_7$)-acyl, phenyl, biphenylyl, O—($CH_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be independently optionally substituted once or twice by F, Cl, OH, $CF_3$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 is ($C_1$–$C_6$)-alkyl, ($CH_2$)$_n$—COOH (where n is 1–4), ($C_3$–$C_6$)-cycloalkyl, ($CH_2$)$_n$-phenyl, ($CH_2$)$_n$-thienyl, ($CH_2$)$_n$-pyridyl or ($CH_2$)$_n$-furyl (where n is 0–5 and the phenyl, thienyl, pyridyl or furyl may each be substituted up to two times by Cl, F, CN, $CF_3$, ($C_1$–$C_3$)-alkyl, OH or O—($C_1$–$C_6$)-alkyl);

R3 is ($C_1$–$C_6$)-alkyl, ($CH_2$)$_n$—COOH (where n is 1–4), ($C_3$–$C_6$)-cycloalkyl, ($CH_2$)$_n$-phenyl, ($CH_2$)$_n$-thienyl, ($CH_2$)$_n$-pyridyl or ($CH_2$)$_n$-furyl (where n is 0–5 and the phenyl, thienyl, pyridyl or furyl may each be substituted up to two times by Cl, F, CN, $CF_3$, ($C_1$–$C_3$)-alkyl, OH or O—($C_1$–$C_6$)-alkyl);

and their physiologically tolerated salts.

The invention also relates to compounds of the formula I in the form of their racemates, racemic mixtures and pure enantiomers, and to their diastereomers and mixtures thereof.

The alkyl, alkenyl and alkynyl radicals in the substituents R1, R1', R2 and R3 may be either straight-chain or branched.

Pharmaceutically acceptable salts are particularly suitable for medical applications because of their greater solubility in water compared with the initial compounds on which they are based. These salts must have a pharmaceutically acceptable anion or cation. Suitable pharmaceutically acceptable acid addition salts of the compounds of the invention are salts of inorganic acids such as hydrochloric acid, hydrobromic acid, phosphoric, metaphosphoric, nitric and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. It is particularly preferred to use the chloride for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in non-therapeutic, for example in vitro, applications.

The term 'physiologically functional derivative' used herein refers to any physiologically tolerated derivative of a compound according to the invention, for example an ester, which is able upon administration to a mammal, such as, for example, to humans, to form (directly or indirectly) such a compound or an active metabolite thereof.

A further aspect of this invention is prodrugs of compounds of the invention. Such prodrugs may be metabolized in vivo to a compound of the invention. These prodrugs may themselves be active or not.

The compounds of the invention may also exist in various polymorphous forms, for example, as amorphous and crystalline polymorphous forms. All polymorphous forms of the compounds of the invention fall within the scope of the invention and are a further aspect of the invention.

All references hereinafter to "compound(s) of the formula (I)" refer to compound(s) of the formula (I) as described above and to the salts, solvates and physiologically functional derivatives thereof as described herein.

The compounds of formula (I) are useful in the treatment of type II diabetes and in the treatment or prophylaxis of obesity. Treatment includes either the prophylaxis or the amelioration of the disorder. In order to achieve the treatment, an effective amount of a compound of formula (I) is administered to a patient in need thereof. An "effective amount" is the amount which achieves the treatment of the specified state.

The amount of a compound of the formula (I), which is an "effective amount," that is necessary to achieve the desired biological effect depends on a number of factors, for example, the specific compound chosen, the intended use, the mode of administration and the clinical condition of the patient. The daily dose is generally in the range from 0.3 mg to 100 mg (typically from 3 mg to 50 mg) per day and per kilogram body weight, for example 3–10 mg/kg/day. An intravenous dose may be, for example, in the range from 0.3 mg to 1.0 mg/kg, which may suitably be administered as infusion of 10 ng to 100 ng per kilogram and per minute. Infusion solutions suitable for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single dose formulations which may be administered orally, such as, for example, tablets or capsules, may contain, for example, from 1.0 to 1000 mg, typically from 10 to 600 mg. In the case of pharmaceutically acceptable salts, the above weight data are based on the weight of the aminothiazole ion derived from the salt. The compounds of the formula (I) may be used for prophylaxis or therapy of type II diabetes or obesity as the compound itself, but they are preferably in the form of a pharmaceutical composition with a pharmaceutically acceptable carrier. The carrier must, of course, be compatible in the sense of compatibility with other ingredients of the composition and not be harmful to the patient's health. The carrier may be a solid or a liquid or both and is preferably formulated with the compound as single dose, for example as tablet, which may contain from 0.05% to 95% by weight of the active ingredient. Further pharmaceutically active substances may likewise be present, including further compounds of the formula (I). The pharmaceutical compositions according to the invention may be produced by one of the known pharmaceutical methods which essentially consists of mixing the ingredients with pharmacologically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of the formula (I) used in each case. Coated formulations and coated slow-release formulations also fall within the scope of the invention. Acid- and gastric fluid-resistant formulations are preferred. Suitable gastric fluid-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, pastilles or tablets, each of which contains a defined amount of the compound of the formula (I); as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely dispersed solid carrier, after which the product is shaped if necessary. Thus, for example, a tablet may be produced by compressing or shaping the powder or granules of the compound, where appropriate with one or more additional ingredients. Compressed tablets may be produced by tabletting the compound in free-flowing form, such as, for example, a powder or granules, where appropriate mixed with a binder, lubricant, inert diluent and/or one (or more) surface-active/dispersing agents in a suitable machine. Shaped tablets may be produced by shaping, in a suitable machine, the compound which is in powder form and has been moistened with an inert liquid diluent.

Pharmaceutical compositions suitable for peroral (sublingual) administration comprise suckable tablets which contain a compound of the formula (I) with a flavoring, normally sucrose, and gum arabic or tragamayth, and pastilles which contain the compound in an inert base such as gelatin and glycerol or sucrose and gum arabic.

Suitable pharmaceutical compositions for parenteral administration comprise preferably sterile aqueous preparations of a compound of the formula (I), which are preferably isotonic with the blood of the intended recipient. These preparations are preferably administered intravenously, although administration may also take place by subcutaneous, intramuscular or intradermal injection. These preparations may preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These may be produced by mixing a compound of the formula (I) with one or more conventional solid carriers, for example cocoa butter, and shaping the resulting mixture.

Suitable pharmaceutical compositions for topical use on the skin are preferably in the form of an ointment, cream, lotion, paste, spray, aerosol or oil. Carriers which may be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal applications may be in the form of single plasters which are suitable for long-term close contact with the patient's epidermis. Plasters of this type suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. As a particular option, the active ingredient may be released by electrotransport or iontophoresis as described, for example, in Pharmaceutical Research, 2 (6): 318 (1986).

The invention also relates to a process for preparing the compounds of the formula I, which comprises obtaining the compounds of the formula I by the procedure shown in the following reaction scheme:

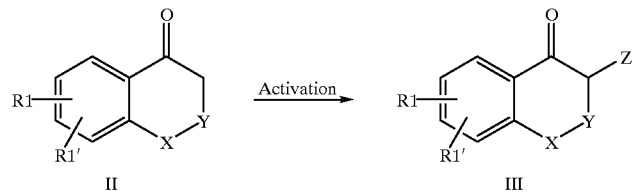

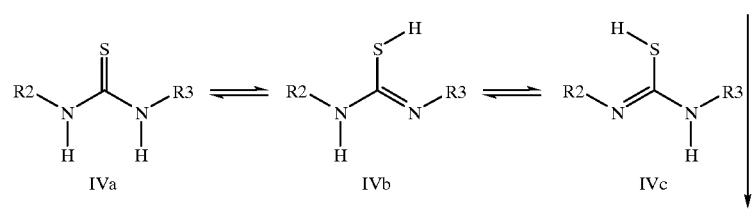

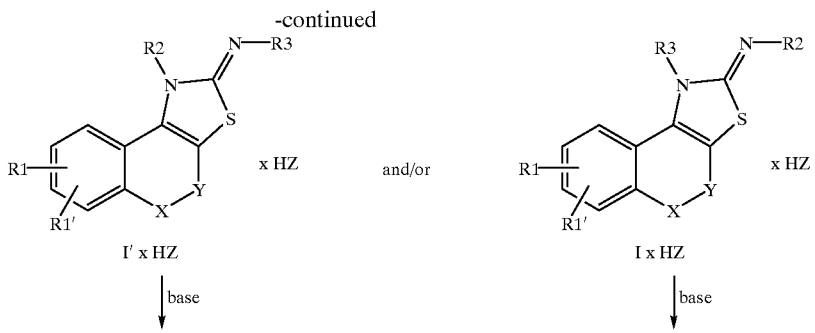

I' x HZ  and/or  I x HZ

| base  | base

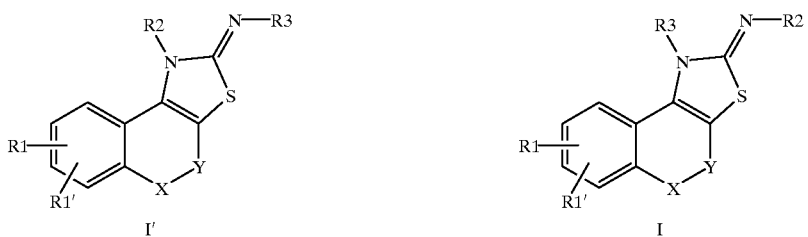

I'  I

For this purpose, compounds of the formula II

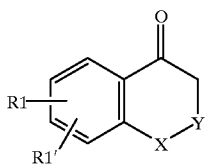

Formula II in which R1, R1', X and Y have the above stated meaning, are activated and converted into a compound of the formula III in which Z is the residue of an activated ester of an inorganic or organic acid.

The compounds of the formula III a re further reacted with thioureas of the formula IVa

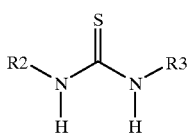

IVa which may be in a tautomeric equilibrium with compounds of the formulae IVb and IVc, and in which R2 and R3 have the stated meanings, to give compounds of the formula I×HZ or I'×HZ', converting, where appropriate, the compounds of the formula I×HZ or I'×HZ with organic or inorganic bases into their free form of the formula I or I'. These in turn may be converted with an inorganic or organic acid into another acid addition salt.

Examples of suitable inorganic acids are: hydrohalic acids such as hydrochloric acid and hydrobromic acid, and sulfuric acid, phosphoric acid and sulfamic acid.

Examples of organic acids which may be mentioned are: formic acid, acetic acid, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethanesulfonic acid, 1,2-benzisothiazol-3(2H)-one, 6-methyl-1,2,3-oxathiazin-4(3H)-one 2,2-dioxide.

The procedure described above is advantageously carried out by reacting the compounds III with the thioureas IVa in the molar ratio of from 1:1 to 1:1.5. The reaction is advantageously carried out in an inert solvent, for example in polar organic solvents such as dimethylformamide, dimethylacetamide, N-methyl-2-pyrrolidone, dioxane, tetrahydrofuran, acetonitrile, nitromethane or diethylene glycol dimethyl ether. However, particularly advantageous solvents prove to be methyl acetate and ethyl acetate, short-chain alcohols such as methanol, ethanol, propanol, isopropanol, and lower dialkyl ketones such as, for example, acetone, 2-butanone or 2-hexanone. It is also possible to use mixtures of the reaction media mentioned; thus, it is also possible to use mixtures of the solvents mentioned with solvents which are less suitable on their own, such as, for example, mixtures of methanol with benzene, ethanol with toluene, methanol with diethyl ether or with tert-butyl methyl ether, ethanol with tetrachloromethane, acetone with chloroform, dichloromethane or 1,2-dichloroethane, it being expedient for the more polar solvent in each case to be used in excess. The reactants may be present in suspension or in solution in the particular reaction medium. It is also possible in principle for the reactants to be reacted without solvent, especially when the particular thioamide has a low melting point. The reaction is only slightly exothermic and may be carried out at between −10° C. and 150° C., preferably between 30° C. and 130° C. A temperature range between 70° C. and 110° C. has usually proved to be particularly favorable.

The reaction time depends substantially on the reaction temperature and is between 2 minutes and 3 days at higher and lower temperatures respectively. In the favorable temperature range, the reaction time is generally between 5 minutes and 48 hours.

The compounds I and I' often separate out in the form of their acid addition salts I×HZ and I'×HZ of low solubility during the reaction, and it is expedient subsequently to add a suitable precipitant. Examples of this which are used are hydrocarbons such as benzene, toluene, cyclohexane or heptane or tetrachloromethane; in particular, alkyl acetates such as ethyl acetate or n-butyl acetate or dialkyl ethers such as diethyl ether, diisopropyl ether, di-n-butyl ether or tert-butyl methyl ether have proved to be particularly suitable. If the reaction mixture is still a solution after the end of the reaction, the salts of the compounds I or I' may, where appropriate after concentration of the reaction solution, be precipitated with one of the precipitants mentioned. It is also possible and advantageous to filter the solution of the reaction mixture into a stirred solution of one of the precipitants mentioned. Since the reaction of the compounds III with the thioureas IVa takes place virtually quantitatively, the resulting crude products are usually already analytically pure. The reaction mixture may also be worked up by making the reaction mixture alkaline by addition of an organic base such as, for example, triethylamine or diisobutylamine or ammonia or morpholine or piperidine or 1,8-diazabicyclo[5.4.0]undec-7-ene, and purifying the crude reaction product after concentration by chromatography, for example on a silica gel column. Examples of eluents which prove to be suitable for this are mixtures of ethyl acetate with methanol, mixtures of dichloromethane with methanol, mixtures of toluene with methanol or ethyl acetate or mixtures of ethyl acetate with hydrocarbons such as heptane. If the crude product is purified in the manner described last, an acid addition product may be obtained from the pure base of the formula I or I' obtained in this way, by dissolving or suspending the base in an organic protic solvent such as methanol, ethanol, propanol or isopropanol or in an organic aprotic solvent such as ethyl acetate, diethyl ether, diisopropyl ether, tert-butyl methyl ether, dioxane, tetrahydrofuran, acetone or 2-butanone, and then adding to this mixture an at least equimolar amount of an inorganic acid such as, for example, hydrochloric acid, dissolved in an inert solvent such as, for example, diethyl ether or ethanol or another one of the inorganic or organic acids mentioned hereinbefore.

The compounds of the formula I and I' may be recrystallized from a suitable inert solvent such as, for example, acetone, 2-butanone, acetonitrile, nitromethane. However, reprecipitation from a solvent such as, for example, dimethylformamide, dimethylacetamide, nitromethane, acetonitrile, preferably methanol or ethanol, is particularly advantageous. The reaction of the compounds of the formula III with the thioureas of the formula IVa may also be carried out by adding an at least equimolar amount of a base such as, for example, triethylamine to the reaction mixture, and then converting, where appropriate, the compounds I or I' obtained in this way into their acid addition products.

Examples of a suitable residue of an activated ester Z in the compounds of the formula III are: Cl, Br, I, O—C(O)—($C_6H_4$)-4-$NO_2$, O—$SO_2$—$CH_3$, O—$SO_2$—$CF_3$, O—$SO_2$—($C_6H_4$)-4-$CH_3$, O—$SO_2$—$C_6H_5$.

The acid addition products I×HZ and I'×HZ may be converted into the compounds of the formula I and I' by treatment with bases. Examples of suitable bases are solutions of inorganic hydroxides such as lithium, sodium, potassium, calcium or barium hydroxide, carbonates or bicarbonates, such as sodium or potassium carbonate, sodium or potassium bicarbonate, ammonia and amines such as triethylamine, diisopropylamine, dicyclohexylamine, piperidine, morpholine, methyldicyclohexylamine.

Thioureas of the formula IVa either are commercially available or may be prepared by methods known from the literature.

Apart from the derivatives described in the examples, also obtained according to the invention are the compounds of the formula I, and their acid addition products, compiled in the following Table 1:

TABLE 1

Examples     Formula I

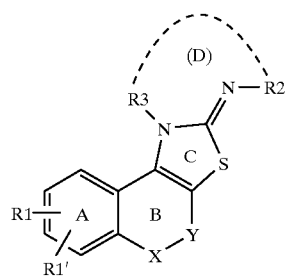

| Ex. | $R_1$; $R'_1$ | $R_2$ | $R_3$ | Y | X | Salt | m.p. [° C.] |
|---|---|---|---|---|---|---|---|
| 1 | 5-$SO_2$-$NH_2$; 6-Cl | $CH_3$ | $CH_3$ | — | $CH_2$ | HBr | 298 |
| 2 | 5-$SO_2$-$NH_2$; 6-Cl | $CH_2$—($C_6H_5$) | $CH_2$—($C_6H_5$) | — | $CH_2$ | HBr | 243 |
| 3 | 6-Cl | $CH_3$ | $CH_3$ | — | $CH_2$ | HBr | 278 |
| 4 | 6-Cl | $CH_3$ | $CH_3$ | — | $CH_2$ | HCl | 281 |
| 5 | 6-Cl | $CH_2$—$CH_2$ | | — | $CH_2$ | HCl | 258 |
| 6 | 6-Cl | $CH_2$—COOH | $CH_3$ | — | $CH_2$ | HBr | 256 |
| 7 | 6-Cl | $CH_2$—COOH | $C_6H_5$ | — | $CH_2$ | HBr | 243 |
| 8 | 5-F | $CH_2$—$CH_2CH_2$—COOH | $CH_3$ | $CH_2$ | O | HCl | 234 |

TABLE 1-continued

Examples Formula I

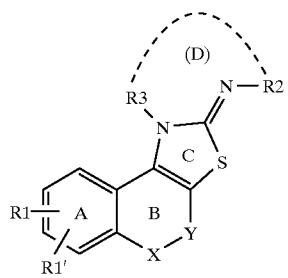

| Ex. | $R_1$; $R'_1$ | $R_2$ | $R_3$ | Y | X | Salt | m.p. [° C.] |
|---|---|---|---|---|---|---|---|
| 9 | 5-F | $CH_2$—COOH | $CH_3$ | $CH_2$ | O | HCl | 256 |
| 10 | 5-$SO_2$—$CH_3$ | $CH_3$ | $CH_3$ | — | $CH_2$ | HCl | 256 |
| 11 | 7-Cl | $CH_3$ | $CH_3$ | — | $CH_2$ | HCl | 250 |
| 12 | 5-Cl | $CH_3$ | $CH_3$ | — | $CH_2$ | HCl | 249 |
| 13 | 6-F | $CH_3$ | $CH_3$ | — | $CH_2$ | HCl | 250 |
| 14 | 6-Cl | $CH_3$ | $CH_3$ | — | $CH_2$ | — | 171 |
| 15 | 6-(O—$C_6H_4$)-4-Cl | $CH_3$ | $CH_3$ | — | $CH_2$ | HCl | 251 |
| 16 | 6-O—$CH_2$—$CF_3$ | $CH_3$ | $CH_3$ | — | $CH_2$ | HCl | 276 |
| 17 | 6-O—$CH_2$—$CF_2$—$CF_3$ | $CH_3$ | $CH_3$ | — | $CH_2$ | HCl | 240 |
| 18 | 7-($C_6H_4$)-4-$CF_3$) | $CH_3$ | $CH_3$ | — | $CH_2$ | — | 231 |
| 19 | 5-($C_6H_4$)-4-Cl) | $CH_3$ | $CH_3$ | — | $CH_2$ | HBr | 256 |
| 20 | 6-(O-$C_6$-$H_4$)-3-$CH_3$) | $CH_3$ | $CH_3$ | — | $CH_2$ | HCl | 229 |
| 21 | 6-O—$CH_2$—$CF_2$—$CF_2$—$CF_3$ | $CH_2$—$CH_2$—$CH_2$ | | — | $CH_2$ | HCl | 271 |
| 22 | 6-O—$CH_2$—$CF_2$—$CF_2$—$CF_3$ | $CH_3$ | $CH_3$ | — | $CH_2$ | HCl | 251 |
| 23 | 6-Cl | $C_6H_5$ | $C_6H_5$ | — | $CH_2$ | HBr | 213 |
| 24 | 6-Cl | ($C_6H_4$)-4-Cl | ($C_6H_4$)-4-Cl | — | $CH_2$ | — | 235 |
| 25 | 6-Cl | ($C_6H_4$)-4-$OCH_3$ | ($C_6H_4$)-4-$OCH_3$ | — | $CH_2$ | HBr | 243 |
| 26 | 6-(O—$C_6H_5$) | $CH_2$—$CH_2$ | | — | $CH_2$ | HBr | 243 |
| 27 | 6-(O—$C_6H_5$) | $CH_3$ | $CH_3$ | — | $CH_2$ | HBr | 205 |
| 28 | 6-(O—$C_6H_4$-3-$CH_3$) | $CH_2$—$CH_2$ | | — | $CH_2$ | HBr | 250 |
| 29 | 6-$CONH_2$ | $CH(CH_3)_2$ | $CH(CH_3)_2$ | — | $CH_2$ | HBr | 243 |
| 30 | 6-Cl | $C_6H_5$ | $CH_2$-$CH_2$-O-$CH_3$ | — | $CH_2$ | HBr | 231 |
| 31 | 6-Cl | $C_6H_5$ | $CH_2$-$CH_2$-$C_6H_5$ | — | $CH_2$ | HBr | 266 |
| 32 | 6-Cl | $CH_3$ | $C_6H_4$-4-C(O)O—$CH_2$-$CH_3$ | — | $CH_2$ | HBr | 223 |
| 33 | 6-($CH_2$)$_6$—OH | $C_6H_5$ | $C_6H_5$ | — | $CH_2$ | — | 119 |
| 34 | 6-($CH_2$)$_6$—OH | $CH_3$ | $CH_3$ | — | $CH_2$ | HCl | 195 |
| 35 | 6-($CH_2$)$_6$—$NH_2$ | $CH_3$ | $CH_3$ | — | $CH_2$ | 2HCl | d. from 230 |
| 36 | 6-($CH_2$)$_6$—$NH_2$ | $CH_3$ | $CH_3$ | — | $CH_2$ | — | d. from 120 |

The compounds of the formula I are distinguished by beneficial effects on lipid metabolism, and they are particularly suitable as anorectic agents. The compounds may be employed alone or in combination with other anorectic active ingredients. Further anorectic active ingredients of this type are mentioned, for example, in the Rote Liste, chapter 01 under weight-reducing agents/appetite suppressants. Examples include, but are not limited to, DECORPA© (from Pierre Fabre Pharma, common name, sterculia), XENICAL© (from Roche, common name orlistat), Antiadipositum X-112S (from Haenseler, common name, D-norpseudoephedrin-HCl), FASUPOND© (from Eu Rho Arzneil, common name, D-norpseudoephedrin-HCl), MIRAPRONT© N (from Mack, Illert., common name, D-norpseudoephedrin-Poly(styrol, divinylbenzol) sulfonate), REGENON© l-retard (from Temmler Pharma, common name, Amfepramon-HCl), RONDIMEN© (from ASTA Medica AWD, common name, Mefenorex-HCl), TENUATE© Retard (from Artegodan, common name, Amfepramon-HCl), Vita-Schlanktropfen Schuck (from Schuck, common name, D-norpseudoephedrin-HCl), VENCIPON© N (from Artesan, common name, Ephedrin-HCl), CEFAMADAR© (from Cefak, common name Madar D4), and Helianthus tuberosus (Plantina). The compounds are suitable for the prophylaxis and, in particular, for the treatment of obesity. The compounds are furthermore suitable for the prophylaxis and for the treatment of type II diabetes.

Biological Test Model

The anorectic effect was tested on male NMRI mice. After withdrawal of feed for 24 hours, the test product was administered by gavage. The animals were housed singly and had free access to drinking water and, 30 minutes after administration of the product, they were offered condensed milk. The consumption of condensed milk was determined, and the general behavior of the animals was inspected, every half hour for 7 hours. The measured milk consumption was compared with that of untreated control animals.

TABLE 2

Anorectic effect measured by reduction in the cumulative milk consumption by treated animals compared with untreated animals.

| | Oral dose [mg/kg] | Number of animals/cumulative milk consumption by the treated animals N/[ml] | Number of animals/cumulative milk consumption by the untreated animals N/[ml] | Reduction in the cumulative milk consumption as % of the controls | Remarks |
|---|---|---|---|---|---|
| R1 = R1' = H, X = $CH_2$, Y = $CH_2$; R2–R3 = $(CH_2)_2$ x HBr (Prior art) | 50 | 5/not analyzable | 5/4.08 | not analyzable | acute toxicity for all animals in the group (fits); 1 animal |
| Example 15 | 50 | 5/0.22 | 5/4.30 | 95 | none |
| Example 16 | 50 | 5/0.24 | 5/3.84 | 94 | none |
| Example 17 | 50 | 5/0.94 | 5/3.84 | 74 | none |
| Example 21 | 50 | 5/0.08 | 5/3.58 | 98 | none |
| Example 22 | 50 | 5/0.08 | 5/4.50 | 98 | none |
| Example 24 | 50 | 5/0.30 | 5/4.26 | 93 | none |

The data from the table shows that the compounds of the formula I exhibit a good anorectic effect. No side effects were observed in the experimental animals.

The examples detailed below serve to illustrate the invention without, however, restricting it. The stated decomposition points are not corrected and generally depend on the heating rate.

PROCEDURE EXAMPLE 1

(6-Chloro-3-methyl-3,8-dihydroindeno[1,2-d]thiazol-2-ylidene)methylamine hydrobromide: (compound of Example 3)

a) 6-Chloro-3-methyl-2-methylimino-2,3,8,8a-tetrahydroindeno[1,2-d]thiazol-3a-ol hydrobromide 2.47 g (10 mmol) of 2-bromo-5-chloro-1-indanone are dissolved in 30 ml of acetone and, at room temperature, a solution of 1.05 g (10 mmol) of N,N'-dimethylthiourea in 10 ml of acetone is added, and the mixture is stirred at room temperature for 5 h. The precipitate is filtered off with suction and dried in vacuo. Crystallization from methanol/diethyl ether results in the hydrobromide of 6-chloro-3-methyl-2-methylimino-2,3,8,8a-tetrahydroindeno[1,2-d]thiazol-3a-ol of melting point 181–183° C.

b) (6-Chloro-3-methyl-3,8-dihydroindeno[1,2-d]thiazol-2-ylidene)-methylamine 3.05 g (10 mmol) of 6-chloro-3-methyl-2-methylimino-2,3,8,8a-tetrahydro-indeno[1,2-d]thiazol-3a-ol hydrobromide are suspended in 20 ml of glacial acetic acid and stirred under reflux for 4 h. The mixture is allowed to cool to room temperature, and the precipitate is filtered off with suction. The hydrobromide of (6-chloro-3-methyl-3,8-dihydroindeno[1,2-d]thiazol-2-ylidene)methylamine is obtained with a melting point of 278° C.

PROCEDURE EXAMPLE 2

(8-Fluoro-1-methyl-1,4-dihydrochromeno[4,3-d]thiazol-2-ylidene-amino)acetic acid hydrochloride (compound of Example 9)

a) N-tert-Butoxycarbonylmethyl-N'-methylthiourea is obtained by reacting 16.8 g of glycine tert-butyl ester hydrochloride in 100 ml of ethyl acetate with 8 g of methyl isothiocyanate and adding 13.8 ml of ethyl acetate. The mixture is stirred at 35° C. for 4 hours and then left to stand at room temperature for 2 days. The precipitate is filtered off, the organic phase is washed with sodium bicarbonate and with sodium chloride solution and, after drying the extraction solution, the solvent is evaporated off in vacuo. The thiourea is obtained as an oil with a pale brownish color.

b) (8-Fluoro-1-methyl-1,4-dihydrochromeno[4,3-d]thiazol-2-ylideneamino)acetic acid hydrobromide is obtained by adding 3.1 g of N-tert-butoxycarbonylmethyl-N'-methylthiourea to a solution of 3.7 g of 3-bromo-6-fluoro-4-chromanone in acetone and then stirring at room temperature for 24 hours and at 40° C. for a further 8 hours. After distillation, the amorphous oily residue is induced to crystallize in ethyl acetate at 0° C. Colorless crystals, melting point 184° C.

c) (8-Fluoro-1-methyl-1,4-dihydrochromeno[4,3-d]thiazol-2-ylideneamino)acetic acid hydrochloride is obtained by boiling 4.3 g of (8-fluoro-1-methyl-1,4-dihydrochromeno[4,3-d]thiazol-2-ylideneamino)acetic acid hydrobromide in 60 ml of glacial acetic acid for 2 hours, then leaving to stand at room temperature for 6 hours, subsequently cooling to about 10° C. and filtering off the crystalline precipitate. It is recrystallized from a mixture of glacial acetic acid and a little water and a few milliliters of aqueous hydrochloric acid, cooling to 0° C. Colorless crystals, melting point 256° C.

PROCEDURE EXAMPLE 3

(5-Methanesulfonyl-3-methyl-3,8-dihydroindeno[1,2-d]thiazol-2-ylidene)methylamine hydrochloride (compound of Example 10)

a) 5-Methanesulfonyl-3-methyl-2-methylimino-2,3,8,8a-tetrahydroindeno[1,2-d]thiazol-3a-ol 1.45 g of 2-bromo-6-methanesulfonyl-1-indanone are dissolved in 15 ml of acetone and, while stirring, 0.65 g of N,N'-dimethylthiourea in 10 ml of acetone is added. The solution is initially clear but, after about 10 min, the hydrobromide of 5-methanesulfonyl-3-methyl-2-methylimino-2,3,8,8a-tetrahydroindeno[1,2-d]thiazol-3a-ol crystallizes out. Stirring at room temperature for 1 h is followed by filtration with suction and washing with a little acetone. 2.1 g of hydrobromide (melting point 265° C.) are suspended in 10 ml of methanol, and 1 ml of triethylamine is added. After 15 min, 150 ml of water is added, and the mixture is stirred while cooling in ice for 1 h. The product which is formed is filtered off with suction and washed with a little cold water. 5-Methanesulfonyl-3-methyl-2-methylimino-2,3,8,8a-tetrahydroindeno[1,2-d]thiazol-3a-ol is obtained with a melting point of 158° C.

b) (5-Methanesulfonyl-3-methyl-3,8-dihydroindeno [1,2-d]thiazol-2-ylidene)methylamine hydrochloride 312 mg of 5-methanesulfonyl-3-methyl-2-methylimino-2,3,8,8a-tetrahydroindeno[1,2-d]thiazol-3a-ol are stirred in 20 ml of 50% concentrated hydrochloric acid at room temperature for 3 h. The mixture is then heated at 60° C. for 1 h. The solution is filtered and cautiously concentrated in vacuo (<60 C) and the remaining residue is stirred with ethanol. Filtration with suction and washing with a little ethanol result in (5-methanesulfonyl-3-methyl-3,8-dihydroindeno[1,2-d]thiazol-2-ylidene)methylamine hydrochloride, melting point >250° C.

PROCEDURE EXAMPLE 4

[6-(4-Chlorophenoxy)-3-methyl-3,8-dihydroindeno[1,2-d]thiazol-2-ylidene]methylamine hydrochloride (compound of Example 15)

6-(4-Chlorophenoxy)-3-methyl-2-methylamino-8,8a-dihydroindeno[1,2-d]thiazol-3a-ol hydrochloride is boiled under reflux in 15 ml of glacial acetic acid for 4 hours, the solvent is removed by distillation under reduced pressure, and the residue is induced to crystallize under diisopropyl ether. Melting point 250–252° C.

PROCEDURE EXAMPLE 5

Methyl[3-methyl-7-(4-trifluoromethylphenyl)-3,8-dihydroindeno[1,2-d]thiazol-2-ylidene]amine hydrobromide (compound of Example 18)

a) 4-(4-Trifluoromethylphenyl)-1-indanone 6.33 g (0.03 mol) of 4-bromo-1-indanone and 5.7 g (0.03 mol) of 4-trifluoromethylphenylboronic acid are suspended with 6.36 g (0.06 mol) of sodium carbonate in a mixture of 100 ml of toluene with 20 ml of ethanol and 20 ml of water. Under an argon atmosphere, 320 mg (1.42 mmol) of palladium(II) acetate and 787 mg (3 mmol) of triphenylphosphine are added, and the mixture is boiled under reflux for 5 h. After the reaction is complete, the ethanol content is evaporated off in vacuo, 50 ml of 0.5 N sodium hydroxide solution are added to the residue, and the mixture is stirred and filtered with suction through a clarifying layer. The organic phase of the filtrate is separated off, shaken 3× with 50 ml of water each time, shaken once with saturated brine, dried over sodium sulfate and concentrated in vacuo. The crude product is chromatographed on silica gel with n-heptane/ethyl acetate 3/1. 4-(4-Trifluoromethylphenyl)-1-indanone is obtained with a melting point of 75–78° C.

b) 2-Bromo-4-(4-trifluoromethylphenyl)-1-indanone 2.76 g (10 mmol) of 4-(4-trifluoromethylphenyl)-1-indanone are dissolved in 20 ml of glacial acetic acid and, after addition of 10 µl of a 48% strength solution of HBr in glacial acetic acid, while stirring a solution of 0.516 ml (10.05 mmol) of bromine in glacial acetic acid is added. After 3 h at room temperature, the reaction mixture is poured into a mixture of 100 ml of water with 100 g of ice and 100 mg of sodium bisulfite, and the resulting suspension is shaken with dichloromethane. The organic phase is washed 3× with water, dried over sodium sulfate, filtered and concentrated in vacuo. The residue is chromatographed on silica gel with dichloromethane/n-heptane 3/1. 2-Bromo-4-(4-trifluoromethylphenyl)-1-indanone is obtained with a melting point of 102–105° C., in addition to a little 2,2-dibromo compound.

c) 3-Methyl-2-methylimino-7-(4-trifluoromethylphenyl)-2,3,8,8a-tetrahydroindeno[1,2-d]thiazol-3a-ol hydrobromide 426 mg (1.2 mmol) of 2-bromo-4-(4-trifluoromethylphenyl)-1-indanone and 130.2 mg (1.25 mmol) of N,N'-dimethylthiourea are dissolved in 10 ml of acetone and stirred at room temperature for 4 h. The precipitate is filtered off with suction, washed with acetone and dried in vacuo. The hydrobromide of 3-methyl-2-methylimino-7-(4-trifluoromethylphenyl)-2,3,8,8a-tetrahydroindeno[1,2-d]thiazol-3a-ol is obtained with a melting point of 202–204° C.

d) Methyl[3-methyl-7-(4-trifluoromethylphenyl)-3,8-dihydroindeno[1,2-d]thiazol-2-ylidene]amine hydrobromide 425.5 mg (1 mmol) of 3-methyl-2-methylimino-7-(4-trifluoromethylphenyl)-2,3,8,8a-tetrahydroindeno[1,2-d] thiazol-3a-ol hydrobromide are suspended in 10 ml of glacial acetic acid and stirred at 100° C. for 3 h. The solvent is then evaporated off in vacuo, and the residue is taken up in water, filtered, washed with water and dried in vacuo. Methyl[3-methyl-7-(4-trifluoromethylphenyl)-3,8-dihydroindeno[1,2-d]thiazol-2-ylidene]amine hydrobromide is obtained with a melting point of 230–233° C.

PROCEDURE EXAMPLE 6

7-Phenoxy-4H,9H-2,3-dihydroimidazo[2,1-b]indeno[1,2-d]thiazole hydrobromide (compound of Example 24)

0.73 g of the appropriate hydrobromide of the 9aH,4aH, 4a-hydroxy derivative is heated in 20 ml of glacial acetic acid at 100° C. for 2 hours, the solvent is distilled off, and the residue is induced to crystallize under diisopropyl ether. Melting point 235° C.

Inventors hereby incorporate by reference in its entirety the priority application DE 19908536.6 filed Feb. 26, 1999.

What is claimed is:

1. A compound of the formula I

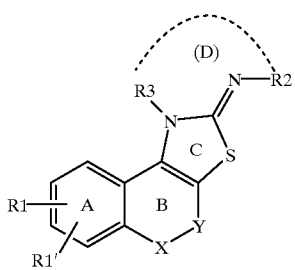

in which

Y is a direct linkage, —CH$_2$— or —CH$_2$—CH$_2$—;

X is CH$_2$ or CH-phenyl;

R1 is F, Cl, Br, I, CF$_3$, NO$_2$, CN, COOH, COO(C$_1$–C$_6$) alkyl, CONH$_2$, CONH(C$_1$–C$_6$)alkyl, CON((C$_1$–C$_6$) alkyl)$_2$, (C$_1$–C$_6$)-alkyl, (C$_2$–C$_6$)-alkenyl, (C$_2$–C$_6$)-alkynyl, O-(C$_2$–C$_6$)-alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$NH(C$_1$–C$_6$)-alkyl, SO$_2$N((C$_1$–C$_6$)-alkyl)$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl (where n is 0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be independently optionally substituted up to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R1' is H, F, Cl, Br, I, CF$_3$, NO$_2$, CN, COOH, COO(C$_1$–C$_6$) alkyl, CONH$_2$, CONH(C$_1$–C$_6$)alkyl, CON((C$_1$–C$_6$) alkyl)$_2$, (C$_1$–C$_6$)-alkyl, (C$_2$–C$_6$)-alkenyl, (C$_2$–C$_6$)-alkynyl, O—(C$_2$–C$_6$)-alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$NH(C$_1$–C$_6$)-alkyl, SO$_2$N((C$_1$–C$_6$)-alkyl)$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$(C$_1$–C$_6$)-alkyl, SO$_2$—(CH$_2$)$_n$-phenyl (where n is 0–6 and the phenyl radical may be substituted up to two times by F, Cl, OH, CF$_3$, NO$_2$, CN, OCF$_3$, O(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be independently optionally substituted up to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)alkyl, N((C$_1$–C$_6$)-alkyl)$_2$, SO$_2$CH$_3$, COOH, COO—(C$_1$–C$_6$)-alkyl or CONH$_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 and R3 together form a —CH$_2$—CH$_2$—, —CH$_2$—C(CH$_3$)$_2$—, —CH$_2$—CH$_2$—CH$_2$— or —CH$_2$CH$_2$—CH$_2$—CH$_2$— group;

and their physiologically tolerated salts and physiologically functional derivatives.

2. A compound of the formula I as claimed in claim 1, wherein

Y is a direct linkage or —CH$_2$—;

X is CH$_2$;

R1 is F, Cl, Br, I, CF$_3$, NO$_2$, CN, COOH, COO(C$_1$–C$_6$) alkyl, CONH$_2$, CONH(C$_1$–C$_6$)alkyl, CON((C$_1$–C$_6$) alkyl)$_2$, (C$_1$–C$_6$)-alkyl, (C$_2$–C$_6$)-alkenyl, (C$_2$–C$_6$)-alkynyl, O—(C$_2$–C$_6$)-alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$—(C$_1$–C$_6$)-alkyl, SO$_2$—(CH$_2$)$_n$-phenyl (where n is 0–6 and the phenyl radical may be substituted up to two times by F, Cl, OH, CF$_3$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$ phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be independently optionally substituted once or twice by F, Cl, Br, I, OH, CF$_3$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), 1,2, 3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R1' is H, F, Cl, I, CF$_3$, CN, COOH, COO(C$_1$–C$_6$)alkyl, CONH$_2$, CONH(C$_1$–C$_6$)alkyl, CON((C$_1$–C$_6$)alkyl)$_2$, (C$_1$–C$_6$)-alkyl, (C$_2$–C$_6$)-alkenyl, (C$_2$–C$_6$)-alkynyl, O—(C$_2$–C$_6$)-alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$NH(C$_1$–C$_6$)-alkyl, SO$_2$N((C$_1$–C$_6$)-alkyl)$_2$, S—(C$_1$–C$_6$)-alkyl, S—(CH$_2$)$_n$-phenyl, SO—(C$_1$–C$_6$)-alkyl SO—(CH$_2$)$_n$-phenyl, SO$_2$(C$_1$–C$_6$)-alkyl, SO$_2$—(CH$_{2n}$-phenyl (where n is 0–6 and the phenyl radical may be substituted up to two times by F, Cl, OH, CF$_3$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)alkyl)$_2$, NH(C$_1$–C$_7$)-acyl, phenyl, biphenylyl, O—(CH$_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be independently optionally substituted once or twice by F, Cl, I, OH, CF$_3$, CN, OCF$_3$, O—(C$_1$–C$_6$)-alkyl, (C$_1$–C$_6$)-alkyl, NH$_2$, NH(C$_1$–C$_6$)

alkyl, N((C$_1$–C$_6$)-alkyl)$_2$, SO$_2$CH$_3$, COOH, COO—(C$_1$–C$_6$)-alkyl or CONH$_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 and R3 together form a —CH$_2$—CH$_2$—, —CH$_2$—C(CH$_3$)$_2$— or —CH$_2$—CH$_2$—CH$_2$— group; and their physiologically tolerated salts and physiologically functional derivatives.

3. A pharmaceutical composition comprising a compound as claimed in claim 1 and a pharmaceutically acceptable carrier.

4. A pharmaceutical composition comprising a compound as claimed in claim 2 and a pharmaceutically acceptable carrier.

5. The pharmaceutical composition of claim 3 further comprising one or more anorectic active ingredients.

6. The pharmaceutical composition of claim 4 further comprising one or more anorectic active ingredients.

7. A method for the treatment of obesity comprising administering an obesity treating effective amount of a pharmaceutical composition of claim 3 to a patient in need thereof.

8. A method for the treatment of type II diabetes comprising administering a diabetes treating effective amount of the pharmaceutical composition of claim 3 to a patient in need thereof.

9. The method of claim 7 further comprising administering at least one other anorectic active ingredient.

10. The method of claim 8 further comprising administering at least one other anorectic active ingredients.

11. A process for producing a pharmaceutical comprising admixing a compound as claimed in claim 1 with a pharmaceutically suitable carrier, and converting this mixture into a form suitable for administration.

12. A method for the treatment of obesity comprising administering an obesity treating effective amount of a pharmaceutical composition of claim 4 to a patient in need thereof.

13. A method for the treatment of type II diabetes comprising administering a diabetes treating effective amount of the pharmaceutical composition of claim 4 to a patient in need thereof.

* * * * *